US007857778B2

(12) United States Patent
de Muinck

(10) Patent No.: US 7,857,778 B2
(45) Date of Patent: Dec. 28, 2010

(54) APPARATUS FOR PHYSIOTHERAPEUTIC TREATMENT

(75) Inventor: Hendrik Jacob de Muinck, Leersum (NL)

(73) Assignee: Contex B.V. (NL)

( * ) Notice: Subject to any disclaimer, the term of this patent is extended or adjusted under 35 U.S.C. 154(b) by 25 days.

(21) Appl. No.: 12/013,915

(22) Filed: Jan. 14, 2008

(65) Prior Publication Data

US 2008/0139986 A1 Jun. 12, 2008

Related U.S. Application Data

(63) Continuation of application No. PCT/EP2006/063776, filed on Jul. 3, 2006.

(30) Foreign Application Priority Data

Jul. 14, 2005 (DE) ...................... 10 2005 032 883

(51) Int. Cl.
*A61F 5/00* (2006.01)
*A61H 1/00* (2006.01)
*A63B 21/00* (2006.01)

(52) U.S. Cl. ................................ 602/32; 601/5; 482/92

(58) Field of Classification Search ..................... 602/4, 602/32–40; 482/100, 137, 50, 91, 124, 131; 601/5, 23, 84, 33, 34, 40
See application file for complete search history.

(56) References Cited

U.S. PATENT DOCUMENTS 4,563,003 A 1/1986 Bugallo et al. .............. 272/118
5,738,613 A * 4/1998 Clayton ....................... 482/47
5,957,876 A * 9/1999 D'Amico ..................... 602/33
6,123,680 A 9/2000 Brummer ....................... 601/5
6,221,037 B1 * 4/2001 Johnson et al. ............... 602/32
6,443,874 B1 * 9/2002 Bennett ....................... 482/44
6,530,893 B1 3/2003 Castelli ....................... 602/32
6,811,541 B2 * 11/2004 Lambert ...................... 602/36
6,846,275 B2 * 1/2005 Chen et al. .................. 482/100
7,131,955 B2 * 11/2006 Price et al. .................... 602/36

FOREIGN PATENT DOCUMENTS

DE 102 14 996 10/2003

OTHER PUBLICATIONS

International Search Report, dated Oct. 26, 2006, 2 pages.

* cited by examiner

*Primary Examiner*—Patricia M Bianco
*Assistant Examiner*—Tarla R Patel
(74) *Attorney, Agent, or Firm*—St. Onge Steward Johnston & Reens LLC

(57) ABSTRACT

The invention relates to an apparatus for treatment, in particular physiotherapeutic treatment, of a part of the human body, in particular an arm, comprising a holder for fixing the body part to be treated, comprising a traction element, which acts on the body part with a predeterminable tension. The tension is applied by one or more weights acting on the traction element via a tension transmitter, it being possible for the tensile force acting on the body part to be varied or stopped at the beginning, during and/or at the end of the treatment by a counteracting force applied by a motor.

17 Claims, 8 Drawing Sheets

APPARATUS FOR PHYSIOTHERAPEUTIC TREATMENT

CROSS-REFERENCE TO RELATED APPLICATIONS

The present application is a continuation of pending International patent application PCT/EP2006/063776 filed on Jul. 3, 2006, which designates the United States and claims priority from German patent application 10 2005 032 883 filed on Jul. 14, 2005, the content of which is incorporated herein by reference.

FIELD OF THE INVENTION

The invention relates to an apparatus for treatment, in particular physiotherapeutic treatment, of a part of the human body, in particular an arm, comprising a holder for fixing the body part to be treated, in particular the lower arm in the region of the elbow, and comprising a traction element, which acts on the body part, in particular on the wrist of the arm, and by means of which a traction of a predeterminable tension, directed in the direction of extent of the body part, in particular the lower arm, is exerted on the body part, in particular the lower arm.

BACKGROUND OF THE INVENTION

Such an apparatus is already known from DE 102 14 996 A1. The apparatus has an elongated apparatus housing. A holder, a traction element and a control console are disposed on the apparatus housing. The elements listed lie one behind the other in the longitudinal extent of the apparatus housing. The holder can be manually displaced in the longitudinal extent of the apparatus housing, since it is disposed on a rail. When the desired position has been reached, the holder can be fixed on the rail by means of a lever screw. The traction element can be displaced from the holder in the direction of the control console by a gear mechanism driven by an electric motor. Consequently, a tensile force can be exerted on an arm restrained in the holder, which is also fixed to the traction element by means of a cuff, since the traction element is displaced from the holder in the direction of the control console. A lower frame is disposed underneath the apparatus housing.

It is an object of the invention to improve the generic apparatus advantageously in terms of its use and to increase the success of the therapy.

SUMMARY OF THE INVENTION

The object is achieved by each individual claim alone and by any combination whatever of each claim with any other claim as desired.

Claim 1 provides first and foremost that the tension is applied by one or more weights acting on the traction element via a tension transmitting means, it being possible for the tensile force acting on the body part, in particular on the wrist, to be varied or stopped at the beginning, during and/or at the end of the treatment by a counteracting force applied by a motor.

The following details are preferred: the traction cable forms the tension transmitting means. The traction cable is guided in particular over a deflecting roller. At least one weight is guided in a standing leg of the apparatus. A traction rod provided with holes is secured to the tension transmitting means, in particular to the traction cable. This traction rod passes through a multiplicity of weight-exerting plates, which are disposed one above the other and are provided with an opening. The weight-exerting plates have coupling openings for a coupling bolt to be passed through. The coupling bolt may be inserted into a coupling opening as far as and into a hole in the traction rod. The coupling bolt arrests a weight-exerting plate and those lying above it on the traction rod. A cuff associated with the traction element is provided for securing the body part, in particular the wrist. The traction element comprises a carriage on which the tension transmitting means acts on one side and a counteracting force transmitting means, in particular in the form of a cable, acts on the opposite side. The counteracting force transmitting means exerts the counteracting force on the traction element. Furthermore, the counteracting force transmitting means may displace the traction element in a motorized manner into an initial position. An electric motor acts on the traction element in order to apply the counteracting force and/or displace the traction element back. The electric motor may be a linear drive, a threaded spindle or a cable winch. The motor drive that applies the counteracting force or brings about the return displacement has a switchable freewheeling mechanism 52, which acts on the traction element. The motor drive applying the counteracting force or bringing about the return displacement acts on the traction element via a coupling that can be released in a damped manner.

Such an apparatus is used for example for treating carpal tunnel syndrome. Treatment with this apparatus can obviate the need for an operation. Since operations always entail risks, treatment of carpal tunnel syndrome with the apparatus represents a good alternative.

Instead of a traction cable, the tension transmitting means may also be formed by a chain, a wire or a lever mechanism. For example, a traction rod could act on the carriage. Instead of the deflecting roller, a deflecting lever could then be provided. For example, the traction rod could act on an arm of an angle lever which is pivotably mounted about an axis. A further traction rod, which can be connected to weights, may be articulated on the other arm of this angle lever. It is also conceivable to transmit the tensile force hydropneumatically. For this purpose, a pneumatic cylinder may act on the carriage. The cylinder is connected by a pipeline or a flexible tube to a further pneumatic cylinder, on which the weights act. The force transmission may take place by means of negative pressure, but with preference by means of positive pressure. The weights then exert a compressive force on the cylinder and the cylinder or piston likewise exerts a compressive force on the carriage. Technically, however, these forces bring about a traction on the arm of the patient.

The counteracting force may also be applied to the carriage by a rope, a wire, a chain or a lever mechanism. It may also be applied to the carriage hydropneumatically. The motor drive is in this case a pump. It is also conceivable to transmit the forces via spindles or worm gear mechanisms.

BRIEF DESCRIPTION OF THE DRAWINGS

The invention just described is explained in more detail on the basis of an exemplary embodiment. In the drawing.

DETAILED DESCRIPTION OF THE INVENTION

Figure 1:
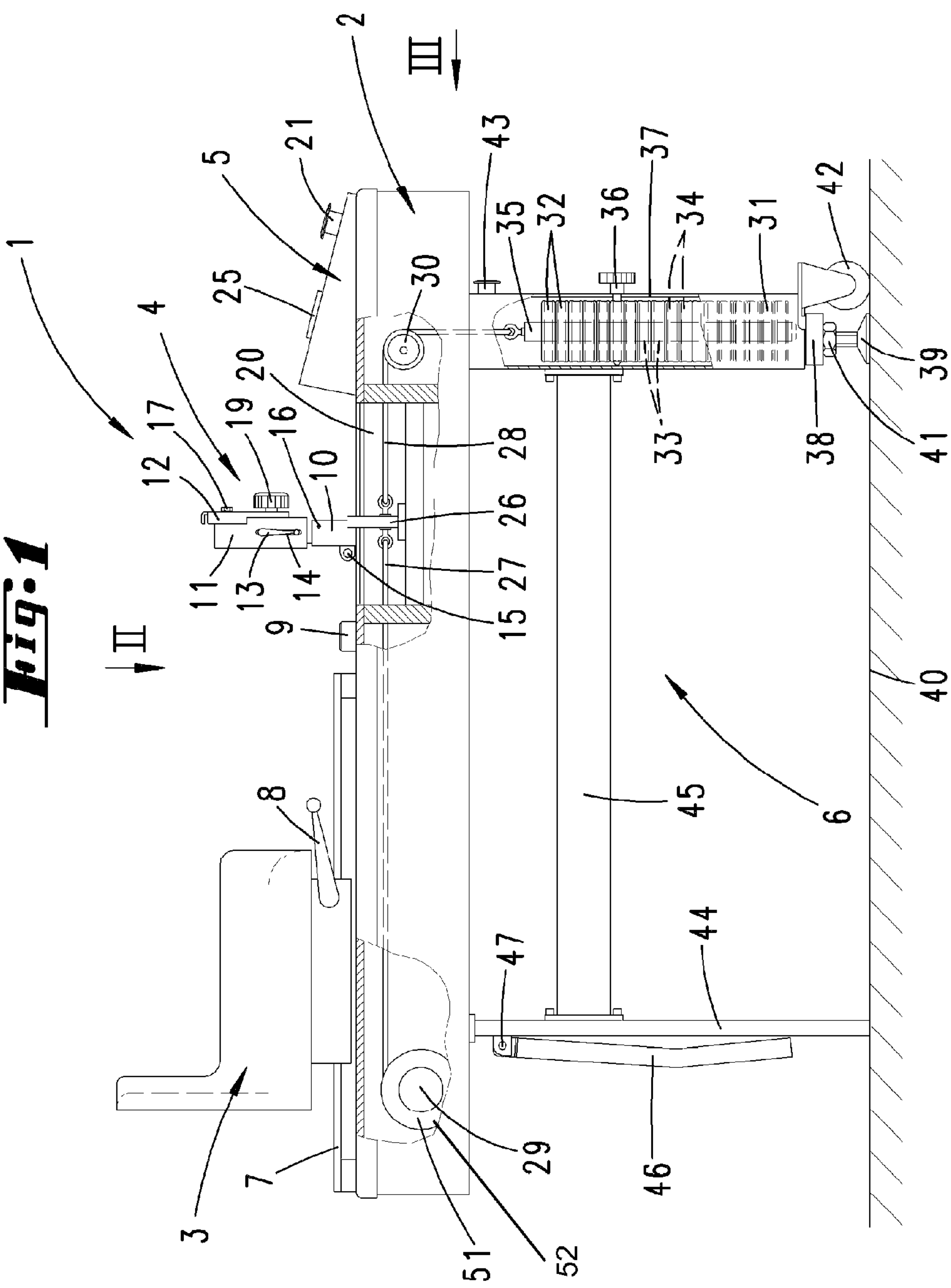
FIG. 1 shows the front view of the apparatus in the starting position, which is represented partly in section.
Figure 2:
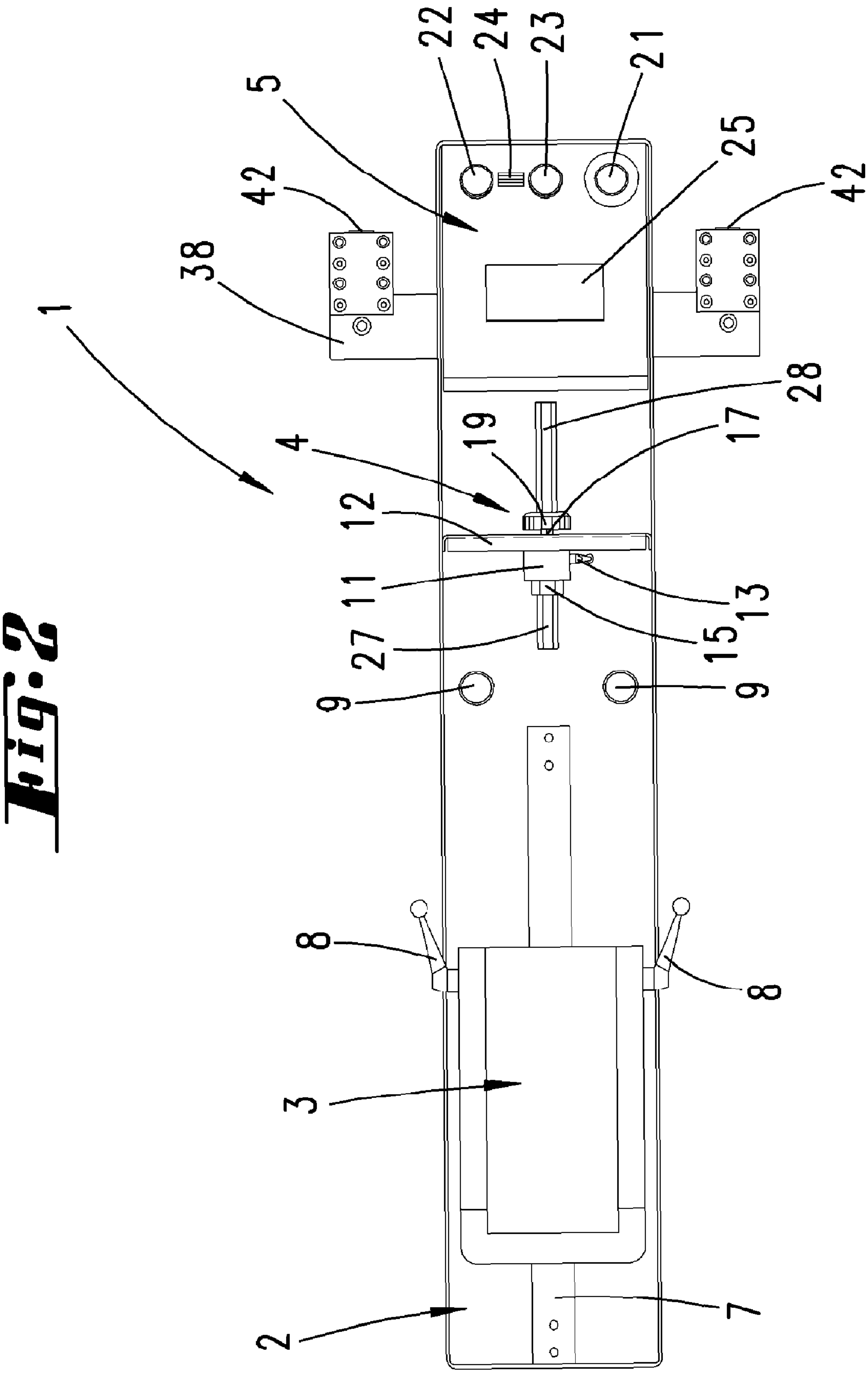
FIG. 2 shows a plan view of the apparatus corresponding to viewing direction II from FIG. 1.
Figure 3:
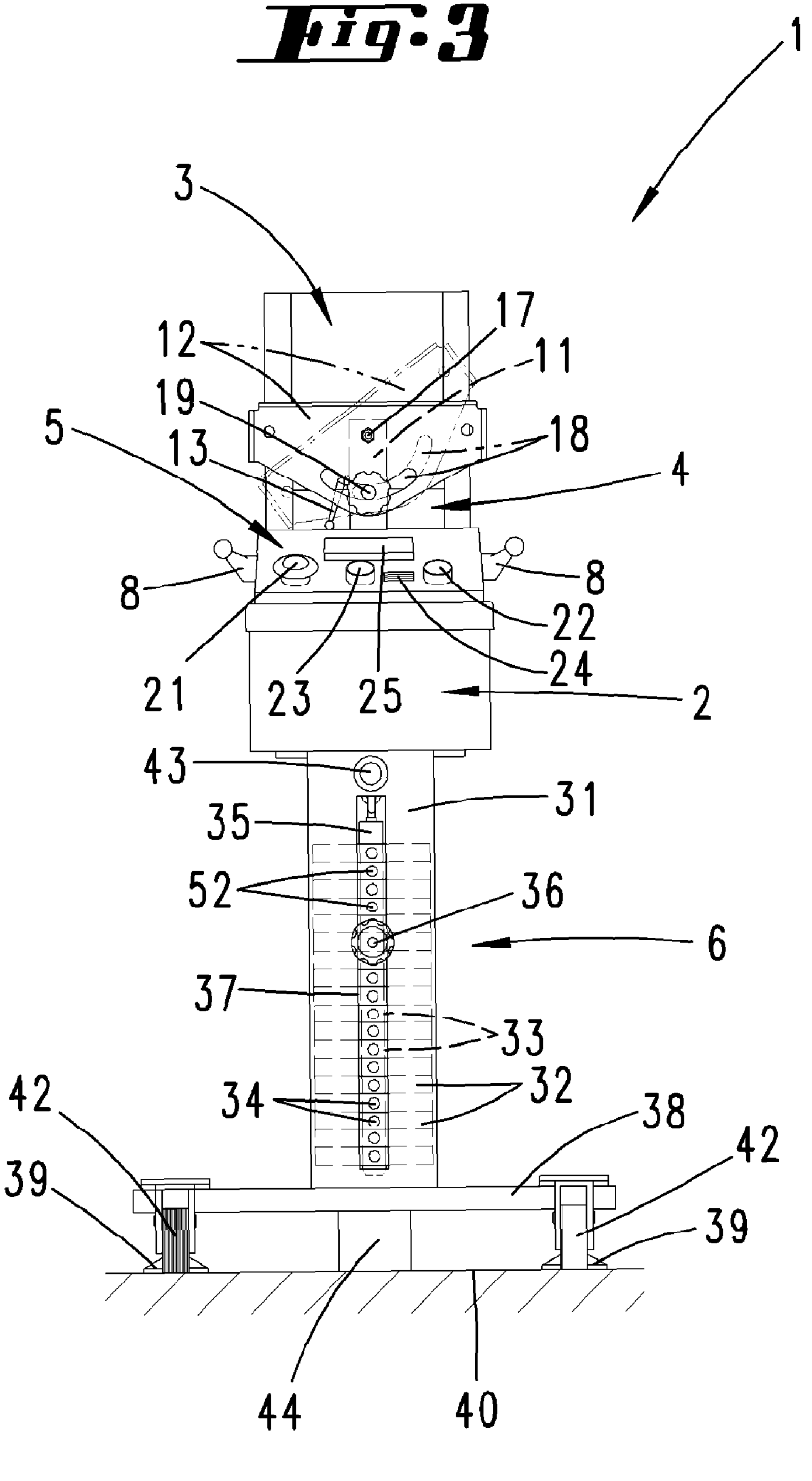
FIG. 3 shows a side view of the apparatus corresponding to viewing direction III from FIG. 1.

The apparatus 1 is represented in FIGS. 1 to 3 in the starting position. The apparatus 1 according to the invention is substantially constructed in the way described in the previously mentioned document of DE 102 14 996 A1. It substantially comprises an apparatus housing 2 with the holder 3, the traction element 4 and the control console 5 disposed on it. A lower frame 6 is disposed underneath the apparatus housing 2.

The elongated apparatus housing 2 has on its upper side a rail 7. One end of the rail 7 lies in the end region of the apparatus housing 2. The rail 7 extends from there to approximately the middle of the longitudinal extent of the apparatus housing 2. In FIG. 1, the end of the rail 7 lies in the left-hand end region of the apparatus 1. The holder 3 is displaceably mounted on the rail 7. It can be displaced in the longitudinal extent of the apparatus housing 2. By means of a lever screw 8, the holder 3 can be fixed in any desired position on the rail 7. In the direction of extent of the rail 7, the latter is followed by two laterally located control buttons 9. They are disposed approximately in the middle of the apparatus 1. By pressing these buttons 9, the patient can interrupt the treatment.

Behind the buttons 9 in the direction of extent of the rail 7 is the traction element 4. This is constructed as in DE 102 14 996 A1. It substantially comprises a pillar 10, a shoe 11 disposed over the latter and a cross bar 12 disposed on that. Disposed to the side of the shoe 11 is a lever screw 13. This protrudes through an oblong hole 14 into a threaded bore of the pillar 10. By means of the lever screw 13, the adjusted height of the shoe 11 can be fixed. Disposed on the pillar 10 in the direction of the holder 3 is a pivot bearing 15. The traction element 4 can be pivoted about this pivot bearing 15 when an overload preventer 16 has tripped. The overload preventer 16 may be formed by a bolt which simply shears off under excessive loading.

As can be gathered from FIG. 3, the cross bar 12 is fixed on the shoe 11 such that it is pivotably movable about a pivot point 17. Disposed underneath the pivot point 17 is an arcuate slot 18. The arcuate slot 18 runs concentrically with respect to the pivot point 17. A tightening screw 19 protrudes through the slot 18 into the shoe 11. With the tightening screw 19, the cross bar 12 can be fixed in any desired angular position in relation to the shoe 11. The maximum angular positions of the cross bar 12 are limited by the respective end of the arcuate slot 18.

The traction element 4 is guided in a longitudinal slot 20. The guidance of the traction element 4 in the apparatus housing 2 may be constructed for example in the way described in DE 102 14 996 A1. The cross bar 12 runs transversely in relation to the longitudinal extent of the apparatus housing 2.

The control console 5 is disposed in the other end region of the apparatus housing 2. In FIG. 3 it can be seen that an emergency-shutdown button 21, an initial button 22, a starting button 23, a buzzer 24 and a display 25 are disposed on the control console 5.

In the event of a malfunction, the apparatus 1 can be immediately switched off by means of the emergency-shutdown button 21. In order to reach the initial position (FIG. 4, FIG. 5) from the starting position (FIGS. 1 to 3), the initial button 22 must be pressed. In order that the treatment can be started, the starting button 23 must be subsequently actuated. The display 25 indicates the individual repetitions in two digits. When a series or the entire treatment has been completed, an acoustic signal emitted by the buzzer 24 is sounded.

Disposed underneath the traction element 4 in the apparatus housing 2 is a carriage 26. The traction element 4 is secured to the carriage 26. It protrudes through the longitudinal slot 20. By means of the carriage 26, the traction element 4 is guided in the longitudinal slot 20. A counteracting force transmitting means 27 acts on the side of the carriage 26 that faces the holder 3. The counteracting force transmitting means 27 is formed by a cable. A tension transmitting means 28 acts on the other side of the carriage 26, which faces the control console 5. This tension transmitting means is likewise formed by a cable. Both cables 27, 28 run in the housing 2 and cannot be seen from the outside.

A motor drive in the form of an electric motor 29 acts on the cable 27. The electric motor 29 drives a cable winch 51. Both are disposed in the end region of the device housing 2 underneath the rail 7. The electric motor 29 and the cable winch 51 are connected to each other via a switchable freewheeling mechanism 52. Furthermore, the coupling between the electric motor 29 and the cable winch 51 can be released in a damped manner.

The cable 28 is guided by means of a deflecting roller 30 in the direction of a standing leg 31 of the lower frame 6. The deflecting roller 30 and the standing leg 31 are disposed underneath the control console 5. The standing leg 31 comprises a hollow body in which weight-exerting plates 32 are disposed one above the other. In the exemplary embodiment, fifteen weight-exerting plates 32 are disposed one above the other. From top to bottom, one weight-exerting plate 32 of 6 kg, six of 1 kg and eight of 1.5 kg are stacked. It is possible to choose 6 kg, from 7 kg to 12 kg in intervals of 1 kg and from 13.5 kg to 24 kg in intervals of 1.5 kg. It is possible to set a weight from 6 kg to 24 kg. The weight-exerting plates 32 have a central opening 33. The openings 33 run in the direction of extent of the standing leg 31, that is to say perpendicular to the direction of extent of the apparatus housing 2. Furthermore, the weight-exerting plates 32 have coupling openings 34. The coupling openings run perpendicular to the openings 33, that is to say in the direction of the longitudinal extent of the apparatus housing 2.

In the starting position of the apparatus 1, a traction rod 35 provided with holes protrudes through each opening 33 of the weight-exerting plates 32. The traction rod 35 has holes 52 at the location of the coupling openings 34. This rod is connected to the tension transmitting means 28. In order to connect the weight-exerting plates 32 to the traction rod 35, a coupling bolt 36 must be inserted into a coupling opening 34 of a weight-exerting plate 32 and through a hole 52 of the traction rod 35. The coupling bolt 36 consequently protrudes through the weight-exerting plate 32 and the traction rod 35. As a result, the weight-exerting plate 32 through which the coupling bolt 36 passes is connected to the traction rod 35. Furthermore, the weight-exerting plates 32 that lie above the coupling bolt 36 are carried along by the traction rod 35. In order that the coupling bolt 36 can be inserted into the weight-exerting plates 32, the standing leg 31 has a longitudinal slot 37.

Disposed underneath the standing leg 31 is a cross beam 38 (FIG. 3). As can be seen in FIG. 1, adjustable feet 39 are provided at the sides of the cross beam 38. These feet can be set by means of the thread in such a way that the apparatus 1 stands securely on the floor 40. In order for the feet 39 to then be fixed, a lock nut 41 is provided. Respectively disposed laterally of the feet 39 in the direction of longitudinal extent of the apparatus 1 is a roller 42. The rollers 42 face toward the end of the apparatus 1 that also accommodates the control console 5. Disposed on the standing leg 31 underneath the apparatus housing 2 is a button 43. The button 43 makes the apparatus 1 move from the initial position (FIGS. 4, 5) into the starting position (FIGS. 1 to 3).

Parallel to the standing leg 31, a further standing leg 44 is disposed underneath the holder 3. The two standing legs 31, 44 are connected to each other by a connecting beam 45. The connecting beam runs parallel to the longitudinal extent of the apparatus housing 2. As can be seen in FIG. 3, the standing leg 44 has a narrower cross-section than the standing leg 31. On the side that is facing away from the standing leg 31, the standing leg 44 has a handle 46. In the basic position (FIGS. 1 to 7), the handle 46 runs approximately parallel to the standing leg 44. Underneath the apparatus housing 2, the handle 46 is articulated in a pivotably movable manner on the standing leg 44 by means of a hinge 47.

In the following section, the operating mode of the exemplary embodiment is explained in more detail:

Starting from FIGS. 1 to 3, the apparatus 1 is in the starting position. In this position, the therapist can choose the weight for the treatment. For this purpose, the coupling bolt 36 has to be inserted into the desired weight-exerting plate 32. This couples the weight of exerting plate 32 to the traction rod 35. Likewise, the weight-exerting plates 32 that are located above the coupling bolt 36 are then also carried along by the traction rod 35. A scale for the weight may be provided for example to be readable from the outside on the standing leg 31.

Figure 5:
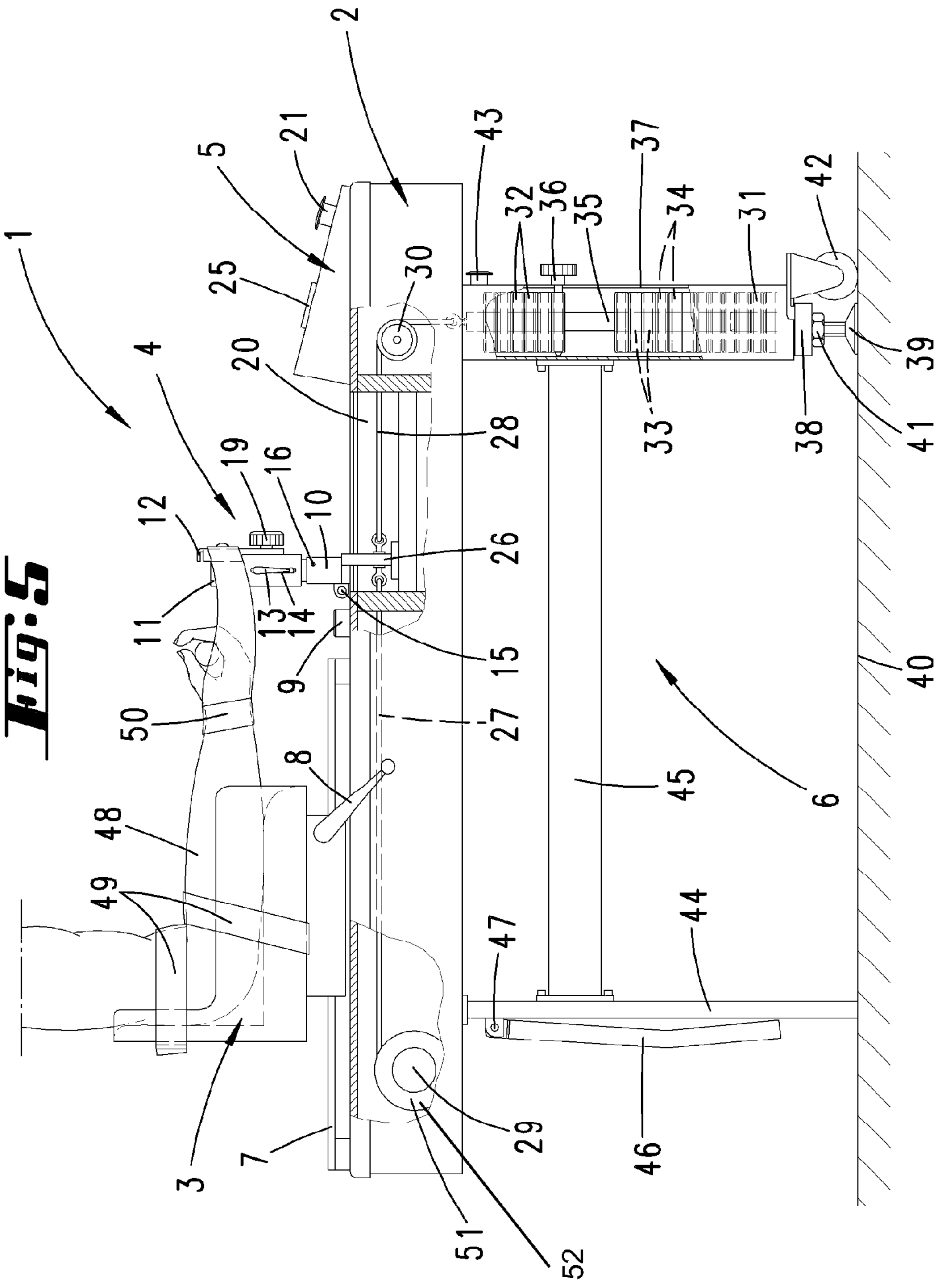
FIG. 5 shows a view corresponding to FIG. 4, but here an arm has been restrained.

In order to displace the apparatus 1 into the initial position, the initial button 22 must be actuated. By actuating the initial button 22, the electric motor 29 is activated. The electric motor 29 acts by means of the cable winch 51 on the cable 27. The rolling up of the cable 27 on the cable winch 51, which is driven by the electric motor 29, has the effect that the carriage 26 with the traction element 4 is displaced as far as possible in the direction of the holder 3. When the traction element 4 has assumed the initial position, the electric motor 29 stops. The displacement path of the carriage 26 with the traction element 4 disposed on it is limited by the longitudinal slot 22. In this position, an arm 48, which is bent at right angles, can be fixed in the holder 3 by means of straps 49. One strap 49 is placed around the upper arm and the other strap 49 is placed around the lower arm. Furthermore, a cuff 50 is placed around the wrist of the arm 48 and then secured to the cross bar 12. In this case, the inner surface of the hand is facing upward. This position is illustrated in FIG. 5. There it can also be seen that the holder 3 is at a distance from the traction element 4 such that the cuff 50 is not yet exerting any tensile force on the arm 48. The position of the holder 3 in relation to the traction element 4 can be varied on the rail 7. The holder 3 is subsequently fixed on the rail 7 with the lever screw 8. The height of the cross bar 12 in relation to the arm 48 can likewise be adjusted. This just requires the lateral lever screw 13 on the shoe 11 to be loosened and then the shoe 11 can be varied in its height. The height variation is limited by the length of the oblong slot 14. Once the desired height has been reached, the shoe 11 can be fixed in its height by means of the lever screw 13.

Figure 6:
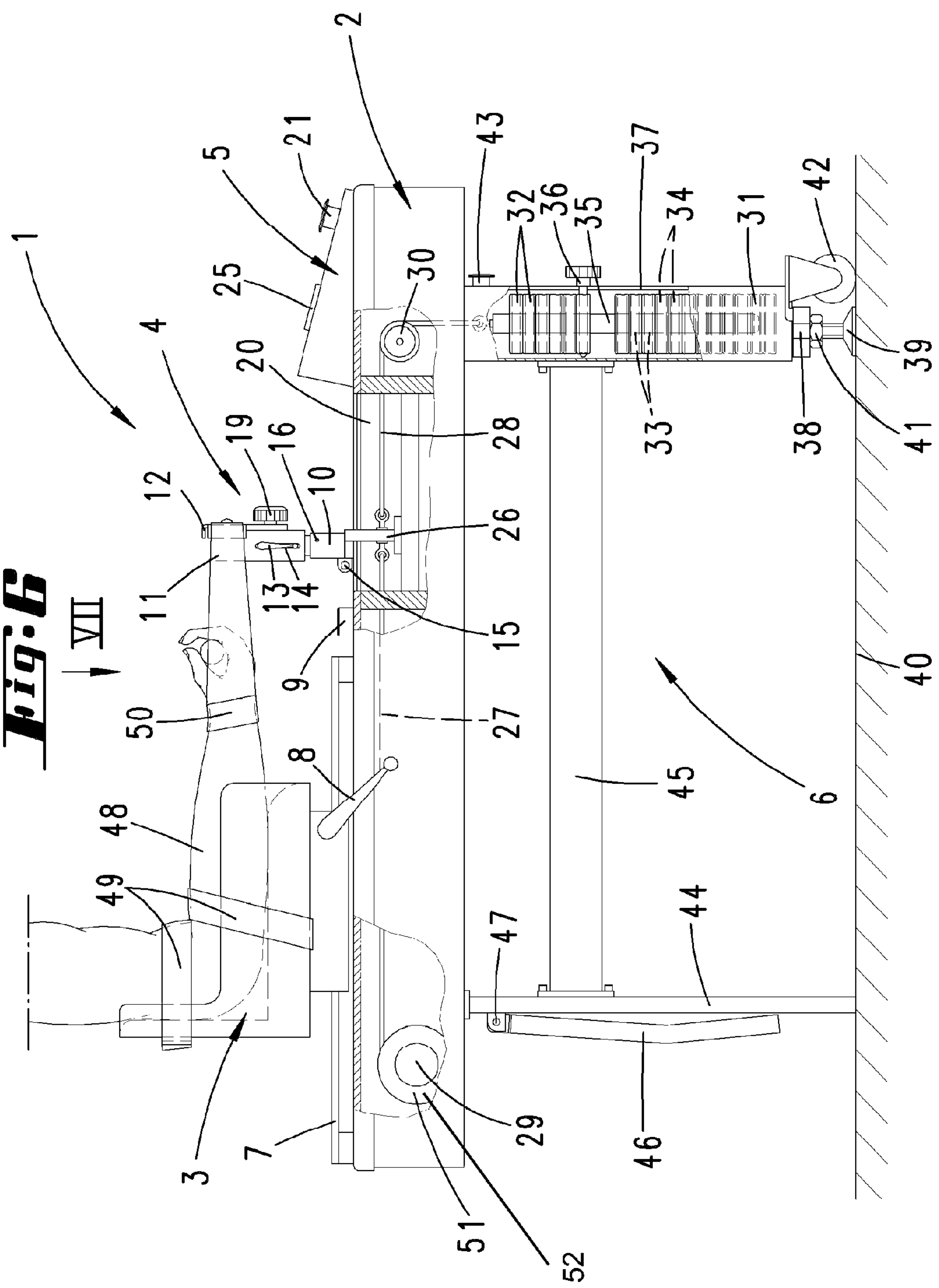
FIG. 6 shows a view corresponding to FIG. 5, the device now exerting a tensile force on the arm (cable 27 is substantially stress-free)
Figure 7:
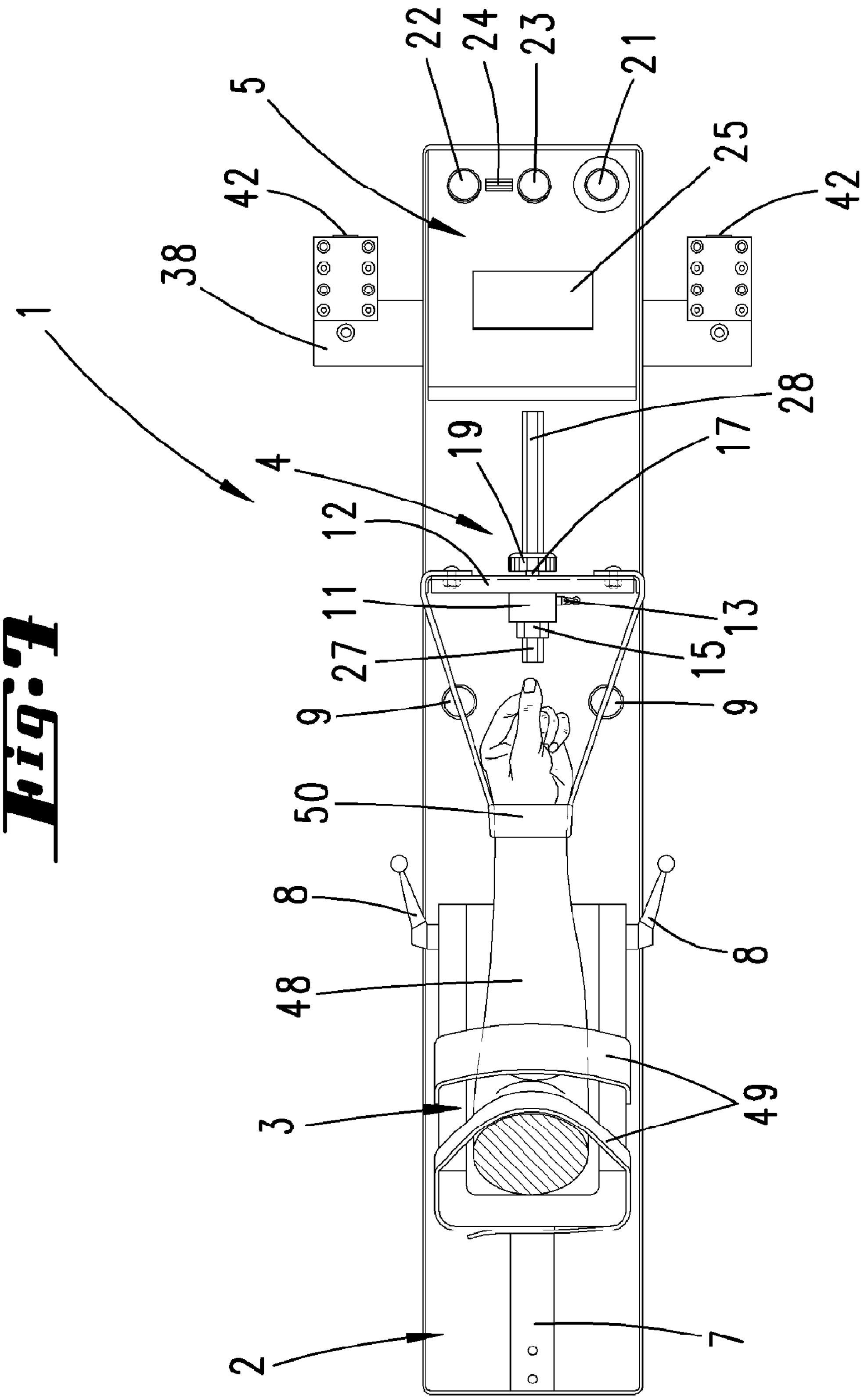
FIG. 7 shows a plan view of the apparatus with a restrained arm, corresponding to viewing direction VII from FIG. 6.

When the apparatus 1 has been set optimally for the patient, the counteracting force transmitting means 27 is slowly released by actuating the starting button 23. This is possible, since the coupling between the electric motor 29 and the cable winch 51 can be released in a damped manner. As a result, the tensile force on the arm 48 builds up only slowly. In FIGS. 6 and 7, the tensile force that is applied by the weight-exerting plates 32 acts on the arm 48. The time between starting the operation and reaching the end position (FIGS. 6, 7) is approximately 7 seconds, with the tensile force being maintained for approximately 2 seconds. Once the time has expired, the electric motor 29 automatically switches on again and, by winding up the cable 27 onto the cable winch, displaces the carriage 26 with the traction element 4 back again into the initial position. After that, the electric motor 29 switches off and the coupling slowly releases the cable roller 51, so that the tensile force can build up once again. This operation is repeated for example ten times. The displacement into the initial position through to renewed starting of the tractive movement takes approximately 5 seconds.

The repetitions are indicated on the display 25. After completion of the ten repetitions, an acoustic signal sounds from the buzzer 24. The apparatus 1 is again in the initial position, which is illustrated in FIG. 5. The position of the cross bar 12 can be changed. This is schematically represented in FIG. 3. As a result, the wrist can be moved into a different position. For this purpose, the tightening screw 19 must be released, and then the cross bar 12 can be pivoted about the pivot point 17. The maximum position of the cross bar 12 is limited by the arcuate slot 18. When the desired position of the cross bar 12 has been reached, the cross bar 12 can be fixed by means of the tightening screw 19. After renewed actuation of the starting button 23, the repetitions, for example ten of them, are carried out once again. After completion of the ten repetitions, the position of the cross bar 12 can be varied again. A customary treatment on this apparatus 1 provides three sets of ten repetitions.

Figure 4:
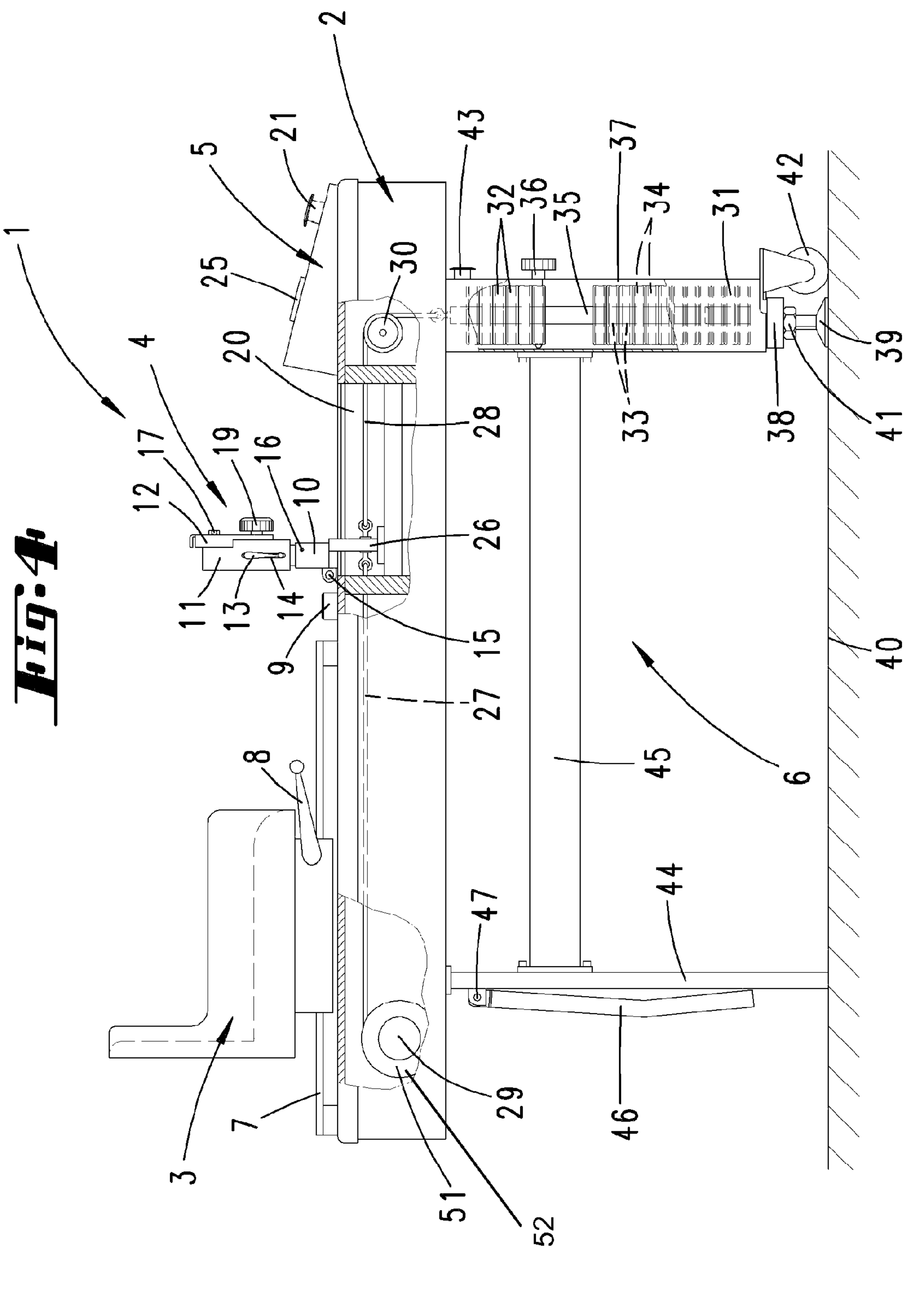
FIG. 4 shows a view corresponding to FIG. 1, but here the traction element has been displaced into an initial position.

The two buttons 9 allow the patient to interrupt the treatment. If the button 9 is pressed, the traction element 4 moves back into the initial position. After renewed pressing of the button 9, the treatment is continued until the ten repetitions have been performed. If a treatment has been completed and a new patient requires a different weight, the button 43 on the standing leg 31 must be actuated from the position that is represented in FIG. 4. Actuating the button 43 makes the electric motor 29 displace the apparatus 1 into the position corresponding to FIGS. 1 to 3. Only in this position is it possible to change the weight without raising the weights.

Figure 8:
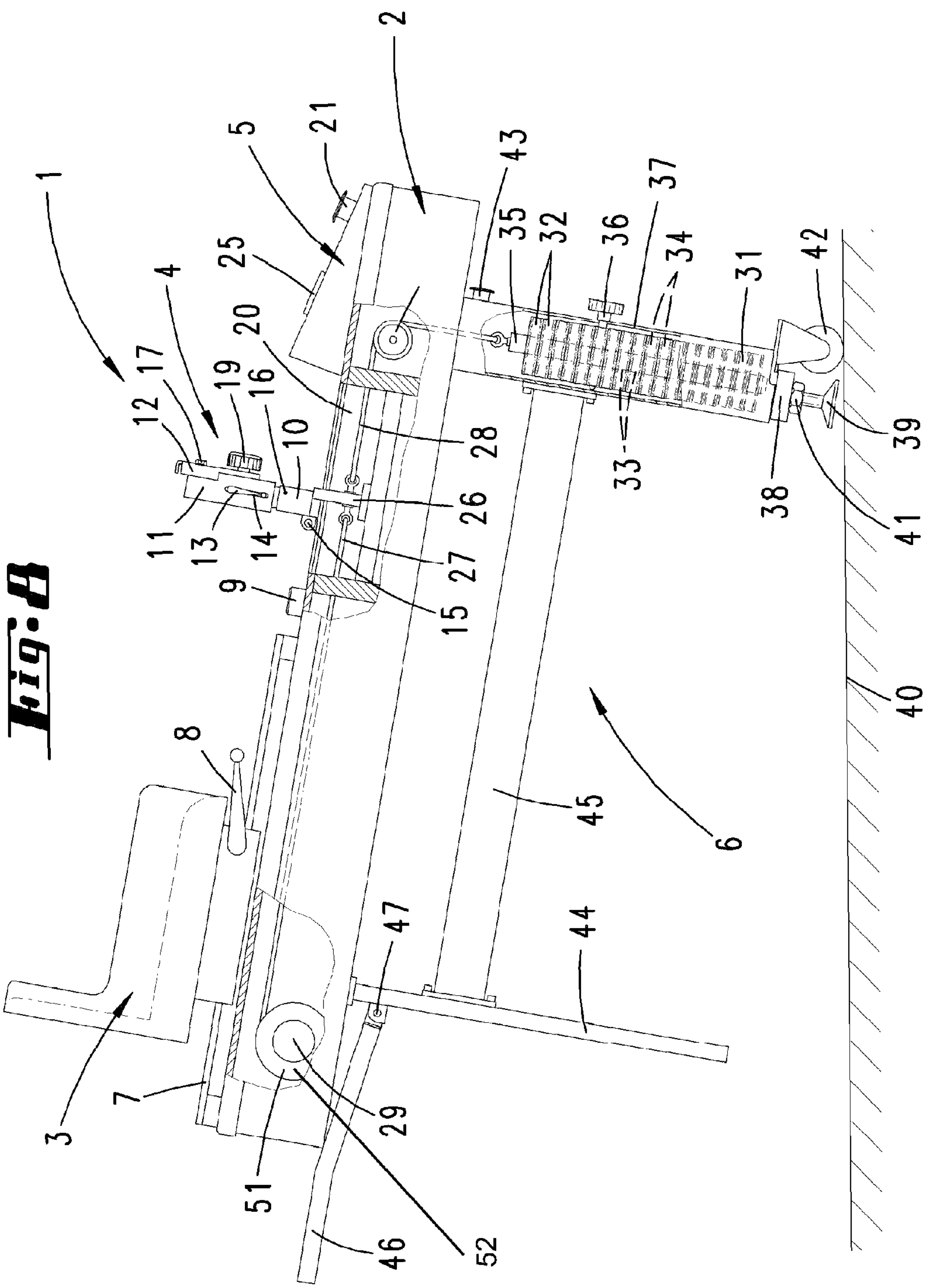
FIG. 8 shows how the apparatus can be transported.

In FIG. 8 it is shown how the apparatus 1 can easily be moved. The handle 46 is pivoted about the pivot point of the hinge 47 such that the handle 46 is positioned approximately at right angles to the standing leg 44. The handle 46 butts against the underside of the apparatus housing 2. The apparatus 1 can then be lifted up by the handle 46. This shifts the weight from the standing legs 31, 44 onto the two rollers 42. In this position, which is represented in FIG. 8, the apparatus 1 can easily be displaced by means of the rollers 42. Once the desired position has been reached, the apparatus 1 is slowly let down and the handle 46 is swung against the standing leg 44. The apparatus 1 can then be aligned by means of the feet 39, which are then fixed by means of a lock nut 41.

As in the previously mentioned DE 102 14 996 A1, the apparatus 1 is likewise fitted with an overload preventer 16 in the traction element 4. If for some reason any kind of excessive load is exerted on the arm 48 during a treatment, the overload preventer 16 trips and allows pivoting of the traction element 4 in the direction of the holder 3 by means of the pivot bearing 15. As a result, the load is removed from the arm 48.

In the case of the exemplary embodiment described above, the tensile force was transmitted to the carriage 26 from the traction rod 35 carrying the weights via a cable 28. However, alternative ways in which the weight force of the weights 32 can be transmitted to the traction element 4 are also conceivable. For example, instead of the traction cable 28, a wire or a chain may be provided. An alternative to the deflecting roller 30 is an angle lever. This angle lever may have two lever arms at right angles to each other. This angle lever can be pivoted about a pivot axis which is associated with the apex of the two lever arms. A traction rod may act on each of the two lever arms. One traction rod is connected to the traction element and the other is connected to the weights. One traction rod may act for example on the carriage 26. The other traction rod may be the traction rod 35 carrying the weights. However, there may also be a coupling rod, which is articulated on the traction rod 35 and is connected to the corresponding arm of the angle lever.

As an alternative to these solutions, the weight force of the weights 32 may also be transmitted to the traction element 4 pneumatically, and in particular hydropneumatically. For this purpose, a pulling piston or a pushing piston of a piston/cylinder unit may for example act on the carriage 26. This piston/cylinder unit is connected via flexible tubes or pipelines to a second piston/cylinder unit, which is acted upon by the weights 32.

In the same way as the tensile force acting on the traction element 4 can act via different force transmitting means, the restoring force that is applied by the electric motor 29 can be transmitted to the traction element 4 via the various force transmitting means. Here, too, a wire or a chain may be used instead of a traction cable 7. The motor 29 may drive a winding drum. However, here it may also be a linear drive. In the same way, here, too, a hydropneumatic drive may be provided for displacing the traction element 4 back in the direction of the holder 3. For this purpose, a piston/cylinder unit may act on the traction element 4, and in particular on the carriage 26. Said unit may comprise a pulling piston or a pushing piston. If the tensile force is also transmitted via a piston/cylinder unit, a double-piston arrangement is suitable here. The restoring force is in this case applied by way of a pump or a second piston/cylinder unit.

As an alternative to the types of drive described above, a geared spindle drive may also be used.

All features disclosed are (in themselves) pertinent to the invention. The disclosure content of the associated/attached priority documents (copy of the prior application) is also hereby incorporated in full in the disclosure of the application, including for the purpose of incorporating features of these documents in claims of the present application.

What is claimed is:

1. An apparatus for treatment, in particular physiotherapeutic treatment of a part of the human body, in particular an arm, comprising:

a holder with at least one strap for fixing an arm to be treated about the lower arm in the region of the elbow;

a traction element, which acts on the wrist of the arm with a traction of a predeterminable tension, pulling the wrist away from the elbow in a first direction;

one or more weights acting on the traction element via a tension transmitting means to apply the predeterminable tension; and a motor connected to a counteracting force transmitting means, the motor acting on the traction element via the counteracting force transmitting means in a second direction, substantially opposite that of the first direction, to apply a counteracting force to the predeterminable tension being applied to the traction element to vary or stop the predeterminable tension acting on the wrist at the beginning, during or at the end of the treatment.

2. The apparatus according to claim 1, characterized in that the tension transmitting means comprises a traction cable, which is guided in particular over a deflecting roller.

3. The apparatus according to claim 1, characterized in that the at least one weight is guided in a standing leg of the apparatus.

4. The apparatus according to claim 1, characterized by a traction rod provided with holes secured to the tension transmitting means, in particular to the traction cable, which traction rod passes through openings of a multiplicity of weight-exerting plates disposed one above the other, which weight-exerting plates have coupling openings for a coupling bolt to be passed through into a hole of the traction rod, in order to arrest the weight-exerting plate and those lying above it on the traction rod.

5. The apparatus according to claim 1, characterized by a cuff associated with the traction element for securing the body part, in particular the wrist, on the traction element.

6. The apparatus according to claim 1, characterized in that the traction element comprises a carriage on which the tension transmitting means acts on one side and a counteracting force transmitting means, in particular in the form of a cable, acts on the opposite side, in order to exert the counteracting force on the traction element and/or to displace the traction element in a motorized manner into an initial position.

7. The apparatus according to claim 1, characterized in that an electric motor acts with a linear drive, a threaded spindle or a cable winch on the traction element in order to apply the counteracting force and/or displace the traction element back.

8. The apparatus according to claim 1, characterized in that the motor applying the counteracting force or bringing about the return displacement acts on the traction element contains a switchable freewheeling mechanism.

9. The apparatus according to claim 1, characterized in that the motor applying the counteracting force or bringing about the return displacement acts on the traction element via a coupling that can be released in a damped manner.

10. The apparatus according to claim 1, characterized by a travel roller, which is provided on a standing leg having the weights and can be brought into contact with the floor supporting the apparatus by tilting the apparatus about the standing leg.

11. An apparatus for treatment, in particular physiotherapeutic treatment of a part of the human body, in particular an arm, comprising:

a holder with at least one strap for fixing an arm to be treated about the lower arm in the region of the elbow;

a traction element, which acts on the wrist of the arm with a traction of a predeterminable tension, pulling the wrist away from the elbow in a first direction;

one or more weights acting on the traction element via a tension transmitting means to apply the predeterminable tension; and a carriage attached to the traction element, wherein the tension transmitting means acts on one side of the carriage in the first direction and a counteracting force transmitting means acts on the opposite side in a second direction, substantially opposite that of the first direction, in order to exert the counteracting force on the traction element.

12. An apparatus for physiotherapeutic treatment, of a part of the human body comprising:

a holder for fixing the body part to be treated;

a traction element having a first side and a second side, which acts on the body part with a predeterminable tension in a first direction;

one or more weights acting on said first side of the traction element providing the predeterminable tension in a first direction via a tension transmitter; and a motor connected to a counteracting force transmitting means, the motor acting on said second side of the traction element via the counteracting force transmitting means for applying a counteracting tensile force in a second direction, substantially opposite that of the first direction, to the traction element to vary or stop the tension applied to the body part by the traction element at the beginning, during, or end of the treatment.

13. An apparatus for physiotherapeutic treatment of an arm of the human body comprising:

a holder displaceably mounted on a rail fixed to a housing, wherein the arm is fixed in the holder bent at an elbow and secured with at least one strap above the elbow and at least one strap below the elbow;

a carriage guided along the housing;

a traction element attached to said carriage, wherein the traction element has a cuff for being secured to a wrist;

one or more weights attached to said carriage via a tension transmitting means, wherein said weights apply a traction force on the carriage in a first direction away from the elbow toward the wrist;

a motor attached to said carriage via a counteracting force transmitting means, wherein said motor applies a counteracting force on the carriage in a second direction, substantially opposite that of the first direction;

a control unit connected to said motor, wherein said control unit varies the counteracting force said motor applies to said carriage in order to release the carriage from an initial position by decreasing the counteracting force to be less than that of the traction force at the beginning of treatment, to increase and decrease the counteracting force during treatment, and to displace the carriage to the initial position at the end of treatment.

14. The apparatus according to claim 13, wherein said traction element is guided along a longitudinal slot in said housing, said longitudinal slot having a first end and a second end, wherein the first end is closer to said holder.

15. The apparatus according to claim 14, wherein when the carriage is in the initial position, said traction element is located closer to the first end of said longitudinal slot.

16. The apparatus according to claim 13, wherein said tension transmitting means and said counteracting force transmitting means are contained in said housing.

17. The apparatus according to claim 13, wherein said control unit is located in said housing, and at least one control button and a display are outside or on said housing.

* * * * *